United States Patent [19]

Hughes

[11] Patent Number: 5,152,394

[45] Date of Patent: Oct. 6, 1992

[54] PERSONAL USE SYRINGE DISPENSING AND COLLECTING SYSTEM

[75] Inventor: David W. Hughes, Chamblee, Ga.

[73] Assignee: McDonald, Withers & Hughes, Inc., Atlanta, Ga.

[21] Appl. No.: 757,449

[22] Filed: Sep. 10, 1991

[51] Int. Cl.⁵ .......................................... B65D 83/00
[52] U.S. Cl. .............................................. 206/366
[58] Field of Search ....................... 206/364, 365, 366

[56] References Cited

U.S. PATENT DOCUMENTS

| | | |
|---|---|---|
| 746,815 | 12/1903 | Ghirardelli . |
| 1,607,923 | 11/1926 | Sebell . |
| 1,643,252 | 9/1927 | McCrery . |
| 3,072,517 | 1/1963 | Gaylord ................. 156/83 |
| 3,086,674 | 4/1963 | Scheuerman ............. 220/24 |
| 3,292,776 | 12/1966 | Penn .................. 206/366 |
| 3,543,996 | 12/1970 | West ................... 229/43 |
| 3,637,072 | 1/1972 | Narusawa et al. ....... 206/63 |
| 4,250,998 | 2/1981 | Taylor ................ 206/570 |
| 4,328,904 | 5/1982 | Iverson ............... 220/256 |
| 4,351,434 | 9/1982 | Elisha ................ 206/366 |
| 4,375,849 | 3/1983 | Hanifi ................ 206/366 |
| 4,454,944 | 6/1984 | Shillington et al. .... 206/366 |
| 4,485,918 | 12/1984 | Mayer ................. 206/366 |
| 4,494,652 | 1/1985 | Nelson ................ 206/366 |
| 4,520,926 | 6/1985 | Nelson ................ 206/366 |
| 4,657,138 | 4/1987 | Watson ................ 206/366 |
| 4,736,844 | 4/1988 | Scott et al. .......... 206/370 |
| 4,767,008 | 8/1988 | Warnecke et al. ....... 206/570 |
| 4,779,728 | 10/1988 | Hanifl et al. ......... 206/366 |
| 4,807,752 | 2/1989 | Chodorow ............. 206/63.5 |
| 4,808,286 | 2/1989 | Angelo ................ 110/246 |
| 4,816,307 | 3/1989 | Honeycutt ............. 428/34.1 |
| 4,828,107 | 5/1989 | Spencer ............... 206/366 |
| 4,842,138 | 6/1989 | Sandel et al. ......... 206/370 |
| 4,848,570 | 7/1989 | Gosciniak ............. 206/366 |
| 4,848,587 | 7/1989 | Nipp .................. 206/571 |
| 4,850,290 | 7/1989 | Benoit et al. ......... 110/46 |
| 4,936,449 | 6/1990 | Conard et al. ......... 206/366 |
| 4,969,554 | 11/1990 | Sawaya ................ 206/370 |
| 4,972,950 | 11/1990 | Shillington ........... 206/366 |
| 4,984,686 | 1/1991 | Shillington ........... 206/366 |
| 5,020,665 | 6/1991 | Bruno ................. 206/366 |
| 5,024,326 | 6/1991 | Sandel et al. ......... 206/366 |
| 5,040,972 | 8/1991 | Kleinheuz et al. ...... 110/242 |
| 5,086,716 | 2/1992 | Lafser ................ 110/346 |

FOREIGN PATENT DOCUMENTS 2040268 1/1980 United Kingdom .

OTHER PUBLICATIONS

The Microban Effect in Health Care Products Inherent Protection Against Hospital Cross-Contamination (leaflet) by Microban Products Co. 1983.
Terminal Laboratory Deodorant (leaflet) by Whitney Products, Inc. (date not available).
Terminal Biohazard System for Laboratory, Hospital & Clinic (leaflet) by Whitney Products, Inc. (date not available).
Pp. 32, 33 & 47 of Pigalog (catalog) by New Pig Corporation (date not available).
Terminal Keepers for Sharps and Broken Glass (leaflet) by Whitney Products, Inc. (date not available).
Sharpsafe Directions for Assembly and Disposal (leaflet) by Concord/Portex, A Smiths Industries Medical Systems Company Jan. 22, 1990.
Syd Syringe and Needle Disposers (leaflet) Bemis Health Care (date not available).
Syd Large Volume Diohazard Disposer (leaflet) Bemis Health Care (date not available).
Sharpsafe Bio-Hazardous Waste Containment System (2 leaf brochure) by Concord Labatories, Inc. (date not available).

Primary Examiner—William I. Price
Attorney, Agent, or Firm—Hopkins & Thomas

[57] ABSTRACT

The container (11) includes a side wall (15) defining a syringe storage chamber (19) where a coiled strip pack (31) of syringes (29) is placed. A central core (35) is place concentrically within the container and forms a collection chamber (20) for used syringes. The side wall (15) includes an outlet opening (30) so that the strip pack (31) can be paid out through the opening (30) and the syringes can be dispensed. The used syringes (29) will be pushed, needle-first through the central opening (26) and into the collection chamber (20), whereby when all the syringes in the strip pack are used and deposited into the collection chamber, the entire container can be disposed of, as by burning.

24 Claims, 3 Drawing Sheets

PERSONAL USE SYRINGE DISPENSING AND COLLECTING SYSTEM

FIELD OF THE INVENTION

The present invention relates in general to a system for dispensing and disposing of hypodermic syringes. More particularly, the invention relates to a home-use system for dispensing, collecting, and disposing of hypodermic needle syringes such as insulin needle syringes used by diabetic persons.

BACKGROUND OF THE INVENTION

Hypodermic needle syringes often are used in a home environment or in other environments away from a medical care facility, such as a work place, or travel environment, by persons for the injection of drugs, such as diabetic patients who must monitor and control their medical condition by insulin therapy, whereby the diabetic receives insulin injections one or more times a day. Typically, the insulin injections are self-administered throughout the course of a day, according to the individual patient's blood sugar or glucose level. Thus it is desirable that the hypodermic needle syringes be conveniently accessible, such as in a home environment or in a purse or luggage.

Disposable, for one-use type hypodermic needles syringes for injecting insulin and other drugs into patients are presently available by prescription from a physician, and typically the syringes are made in a uniform shape and size. The standard disposable syringe employs a plunger which is drawn back from one end of the syringe barrel to fill the syringe through the needle, which is held within a vial of insulin or other liquid drug during a filling operation of the syringe. It is desirable that the hypodermic syringe be sterile and easily accessible and provided to the user in a safe manner, and after injection, the used insulin needle syringes should be safely collected and disposed of without presenting the hazard of inadvertent puncture or scratch of the skin of the user or of others.

Presently, none of the known prior art discloses a practical, safe and inexpensive dispenser and collector designed specifically for home use and portable out of home use dispensing and disposing of hypodermic syringes, such as insulin syringes used by diabetic patients. Thus, diabetics and other persons requiring injections away from a medical facility usually carry the insulin needle syringes in a pre-packaged supply, such as from a bag purchased from a local pharmacy. After use, the used insulin syringes typically are discarded in a generic collector, such as a cardboard box or plastic milk jug, or are discarded directly into a household garbage can or public refuse collector which usually is delivered to a local refuse collection facility. During the containment of the needle syringes, there is a hazard that others including family members, or workers who are handling the garbage of diabetics, and the like might become contaminated by skin scratch or puncture by the needle of the hypodermic syringe.

For example, an unused, prepackaged hypodermic syringe supply can drop or fall from a medicine cabinet or a counter within the household and the syringes can become contaminated when they are exposed to the external environment. Also, if the used syringes are deposited in a generic household collector, such as a cardboard box or milk jug and thrown into the household garbage bag, when the garbage is filled with household trash, the needle of a syringe can protrude through its generic collector and other garbage to scratch or puncture a family member who is transporting the garbage from a room in the household or scratch or puncture a worker who is collecting the trash from a residence, etc. Therefore, it would be desirable to provide a disposable, puncture-resistant, leak-resistant container designed, sized and shaped for safely dispensing new, sterile unused hypodermic syringes one at a time, and after the syringes have been used for collecting the used syringes in the same container, so that the syringes can be carried in and used in a personal environment, such as a home, work place, or travel environment.

SUMMARY OF THE INVENTION

Briefly described, the present invention comprises a system for supplying and dispensing new hypodermic syringes in a personal environment, and after the syringes have been used, for collecting and later disposing of the hypodermic syringes. A preferred embodiment of the invention comprises a puncture-resistant, leak-resistant, cylindrically-shaped container. The new, unused needle syringes are individually packaged in a strip pack in which the syringes are oriented parallel to one another and the strip pack is arranged in a coil and the coiled strip pack is contained within a syringe storage chamber of the cylindrical container. The strip pack is perforated between the syringes so that the syringes are held together in a prearranged sequence before use, yet the syringes become singly accessible when needed by the diabetic by tearing one blister package of the strip pack away from the rest of the strip pack. The side wall of the container includes an outlet opening from the syringe storage chamber for the sequential passage therethrough of the syringes in the strip pack. The outlet opening comprises a flap which is formed by the side wall of the container. This embodiment allows the new, unused syringes to be dispensed one at a time from the syringe storage chamber.

Additionally, an opening is formed at an end wall of the container for passage therethrough of the used syringes to a collection chamber located in the center of the coiled strip pack. Thus, a strip pack of needle syringes is placed within the syringe storage chamber and a free end of the strip pack is paid out through the side outlet opening to dispense the unused hypodermic syringes, and after use, the used hypodermic syringes can be pushed from outside the container through the center opening of the end wall and into the space formed by the central portion of the coiled strip pack of needle syringes, which is the collection chamber of the syringes.

Another preferred embodiment of the invention comprises the same general configuration as the above described embodiment, including a collection chamber for used syringes being formed by an internal cylindrical-wall positioned in the space formed by the central portion of the strip pack with the used hypodermic syringes stored within the internal breadth of the cylindrical-wall. The space between the rigid cylindrical wall and the side wall of the container defines the syringe storage chamber for the unused needle syringe strip pack.

Another embodiment of the invention comprises the same general configuration as described above, but the internal cylindrical wall replaced with a spiral core member with the strip pack arranged in a coil configuration about the core member. This spiral core member is radially expandable and is aligned with the opening of an end wall so that used hypodermic syringes can be pushed along their lengths from outside the container through the opening of the end wall and into the core member within the syringe storage chamber. This space-saving embodiment is particularly desireable because the core member is radially expandable to accept more used needle syringes as the strip pack of syringes is dispensed from about the core member in the syringe storage chamber. Thus, the size of the container corresponds according to the number of syringes in the strip pack.

The above-described embodiments of the invention all comprise a container having a side opening for dispensing the strip pack of unused syringes and an end opening for requiring the used syringes to be stored away from the side opening.

Any of the above-described embodiments of the invention all can also include a supply attachment with cylindrical side wall of sufficient internal breadth to fit snugly about a cylindrical side wall of the container in a piggy-back arrangement. This supply attachment is particularly desirable for storing necessary items, such as insulin vial supplies, alcohol swabs, and glucose test kits which accompany the use of insulin syringes. Thus, the supply attachment would provide the diabetic a complete portable system for dispensing, using and disposing of personal-use insulin syringes.

Any of the above mentioned embodiments of this invention can be used with a mounting bracket which is intended to be affixed to a vertical wall or horizontal surface. The mounting bracket comprises a hollow support means of internal breadth to be inserted into the opening of the end wall of the container, and a support member for supporting the other end wall of the container, thereby mounting the container to a designated area for dispensing, and disposing of insulin syringes. The new syringes are pulled from the sidewall opening of the container by pulling the strip pack, and the used syringes are pushed needle-first through the hollow support means of the mounting bracket back into the collection area of the container.

The material of fabrication for the container can be non-biodegradable, thermoplastic resins, namely polypropylene, polyethylene, polystyrene, acrylonitrile-butadiene-styrene (ABS), polycarbonate. Such materials can form the container by conventional means such as injection molding.

Preferably, however, the container can be fabricated of a biodegradable and combustible material, selected from the group consisting of: natural cellulosic materials, namely paper stock, cardboard, fiberboard, particle board, non-natural cellulosic materials, namely rayon and cellophane, and other materials, namely rubber and natural wax. In addition, the quantity of material that forms the container can be matched with the volume of the syringe storage chamber so that the chamber will receive a predetermined number of needle syringes, and if burned, the material of the container is sufficient to emit enough heat upon combustion to transform the hypodermic syringes in the chamber into a substantially noncontaminated and noncombustible ash.

It is therefore an object of the present invention to provide an apparatus which dispenses new, unused hypodermic needle syringes, and after the syringes have been used, contains the used syringes safely and conveniently in a personal environment such as in a home, car, or work place.

Another object of the present invention is to provide a container which is suitably sized, shaped and placed to dispense new hypodermic syringes and to receive used syringes in predetermined amounts in a non-medical facility environment.

It is yet another object of the present invention to provide a wall-mount to conveniently station the personal use syringe dispensing and disposing system.

Another object of the present invention is to provide a supply attachment to the above-described system forming a complete, one-stop station for insulin syringe users.

A further object of the present invention is to provide a system for safely dispensing, collecting and disposing of hypodermic needle syringes, whereby the container is formed of a puncture-resistant and leak-resistant material.

Another object of the present invention is to provide a container of the type described which can be formed of plastic materials.

It is yet another object of the present invention to provide a container of the type described which can be fabricated of a combustible and biodegradable material so that if incinerated, will not evolve toxic substances to the environment.

It is yet another object of the present invention to provide a container designed to hold a predetermined number of hypodermic needle syringes with the material of the container being combustible and capable of incinerating the syringes stored in the container.

Other objects, features and advantages of this invention will be understood from reading the following specification when taken in conjunction with the accompanying drawings.

DETAILED DESCRIPTION OF THE INVENTION

Figure 1:
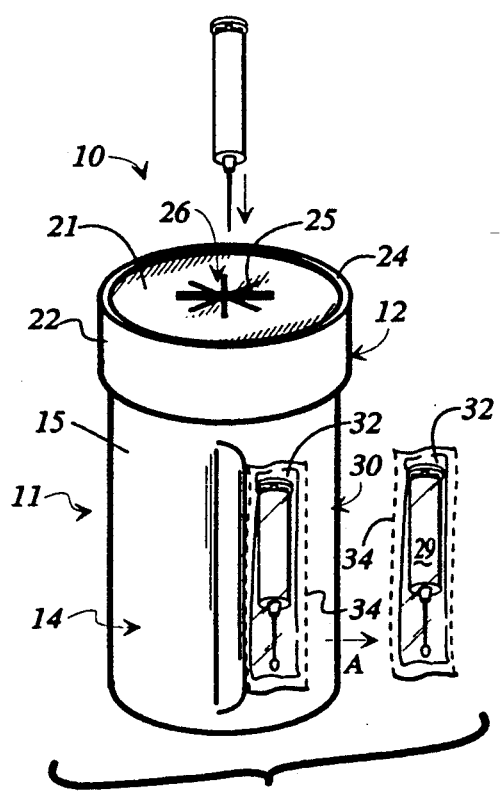
FIG. 1 is a perspective view of the container system for dispensing and disposing of hypodermic needle syringes, showing the free end of the strip pack of syringes at the side opening of the container.
Figure 2:
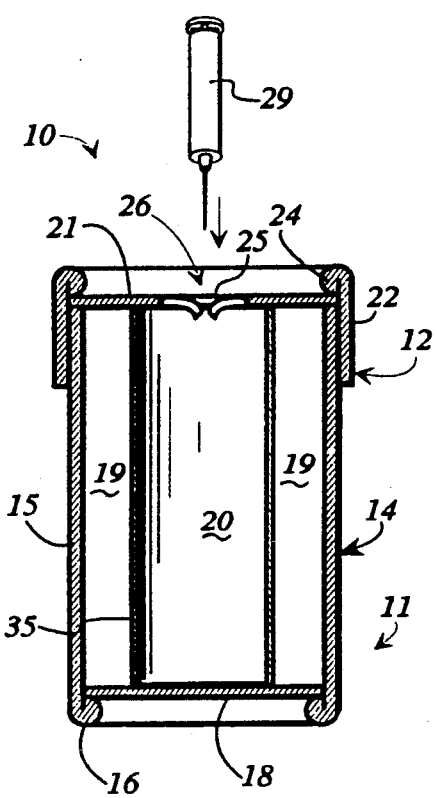
FIG. 2 is a side cross-sectional view of the container system of FIG. 1, with the syringes removed from the container.

Referring now in more detail to the drawings in which like numerals indicate like parts throughout the several views, FIGS. 1 and 2 illustrate a hypodermic needle syringe dispensing and disposing system 10, which includes a cylindrical container 11. The container 11 comprises an upper telescoping cover 12 which telescopes about a lower cylindrical body 14. The lower cylindrical body 14 includes a cylindrical side wall 15 with the lower end portion of the side wall 15 turned inwardly to form a circular flange or seat 16, and a disc-shaped bottom wall 18 is positioned inside the side wall 15 and is supported by the seat. The cylindrical side wall 15 and bottom wall 18 define a syringe storage chamber 19 and a syringe collection chamber 20 which is bound by a top wall means 21 of the telescoping cover 12 (FIGS. 1 and 2).

Figure 5:
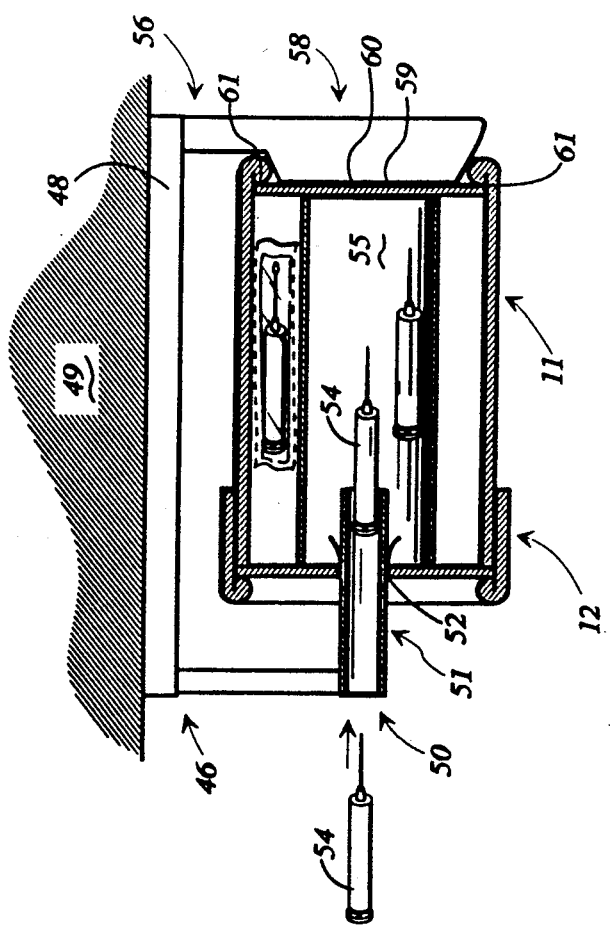
FIG. 5 is a side cross-sectional view of the container system supported by a mounting bracket.

The telescoping cover 12 has a cylindrical side wall 22 which is of sufficient internal breadth to tightly fit over and about an upper end of the cylindrical side wall 15 as shown in FIGS. 1, 2, and 5. The telescoping cover 12 includes an inwardly projecting circular seat 24 supporting the top wall means 21. The top wall means 21 has a scored portion 25 which when broken forms an opening 26 that is of sufficient internal breadth, size, and shape for receiving hypodermic syringes 29 (FIGS. 1 & 2). The top wall means 21 and the bottom wall 18 of the container 11 are spaced a distance greater than the lengths of the syringes so as to allow easy dispensing and disposal of the syringes.

Figure 3:
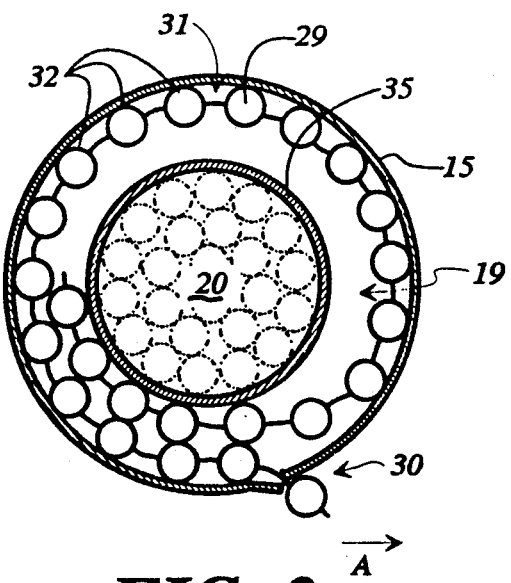
FIG. 3 is a cross-sectional view of the embodiment of FIG. 1 showing the strip pack coiled about an internal cylindrical wall and used syringes stored.

The cylindrical side wall 15 of the cylindrical body 14 has an outlet opening 30 in the side wall 15 for containing a coiled strip pack 31 (FIG. 3) within the syringe storage chamber 19 (FIGS. 2 and 3). The coiled strip pack 31 comprises a series of attached vacuum-packed blister packs 32 which contain unused, sterile hypodermic syringes in a spaced, longitudinal orientation, and the strip pack has perforations 34 between each individual blister pack for individually releasing one blister pack at a time from the strip pack. The strip pack can also include indicia, such as numbering each blister pack of unused hypodermic syringes so as to determine the number of unused syringes left in the strip pack.

An inner cylindrical wall 35 is spaced from the cylindrical side wall 15 of the container 11, and serves as a divider between the syringe storage chamber 19, whereby unused, sterile blister packs 32 of syringes 29 are dispensed from the strip pack through the outlet opening 30 in the direction of arrow A (FIGS. 1 and 3), and the collection chamber 20, whereby after use the syringes 29 are deposited needle-first through the opening 25 in the top wall 21 and into the collection chamber 20 (FIG. 2).

Figure 4:
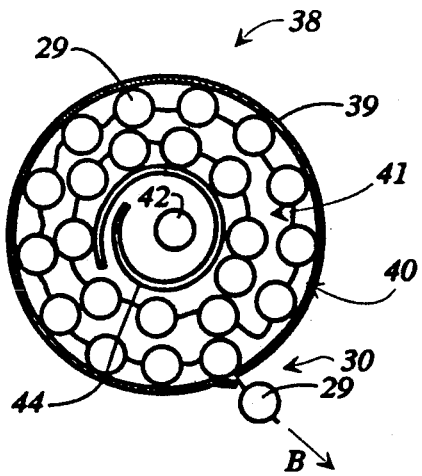
FIG. 4 is a cross-sectional view of another embodiment of the container system, showing the strip pack of syringes coiled about a radially expandable internal spiral core member.

FIG. 4 is another embodiment 38 of the invention comprising the same general exterior configuration as FIGS. 1-3, including a cylindrical exterior side wall 39 containing a storage chamber 40 for storing a strip pack 41 of unused, sterile hypodermic syringes 29 and used syringes 42. This embodiment includes a spiral core member 41, which is radially expandable and aligned with the opening of the top wall of the container, so that used syringes can be pushed along their lengths from outside the container, needle first, through the opening of the top wall and into the core member within the chamber, and the core member radially expands to accept more used needle syringes as the strip pack of syringes is dispensed in the direction of arrow B from about the core member in the chamber. Space efficiency is the main advantage of this embodiment whereby the size of the container is tailored for a designated number of syringes.

FIG. 5 illustrates a wall-mount 46 for securing the container 11 in a convenient location. The wall-mount comprises a mounting bracket 48, preferably attached in a conventional manner to a wall 49 or other appropriate surface by multiple screws or adhesive (not shown). A hollow cylindrical support member 50 has a hollow neck 51 which extends inwardly from the support member, and is sized and shaped so that the opening of the end wall of the container 52 can be mounted about the hollow support member and the hollow support member can serve as a chute for a hypodermic syringe 54 to be deposited into the collection chamber 55 for used syringes. A flexible support member 56 with a cylindrical support arm 58 extending downwardly and having an inwardly oriented protrusion 59 extends adjacent an end wall 60 of the container. The cylindrical support arm 58 is formed of a flexible material so as to releasibly engage the end wall 60 of the container. The protrusion 59 supports the container by an inwardly projecting seat 61 configuration of the container. Therefore, the wall mount provides the convenience of interchanging new containers when the used containers are filled with used syringes.

Figure 6:
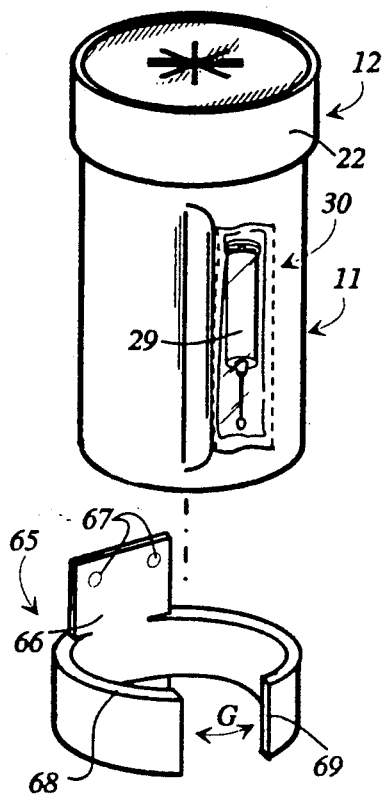
FIG. 6 is a perspective view of the container system being inserted into another mounting bracket.

FIG. 6 illustrates another mounting bracket means 65 for securing the container 11 in a convenient location. The mounting bracket means 65 comprises a bracket 66, which can be preferably attached to a convenient surface by screws or other fastener means 67. The bracket 66 support circular sleeve 68 having a gap G in a portion 69 of the circular sleeve 68 for allowing the user to access the outlet opening 30 for the strip pack of the container. The circular sleeve 68 is positioned in an upright attitude and is of sufficient internal breadth to sustain the container 11 by supporting the cylindrical side wall 22 of the telescoping cover 12.

Figure 7:
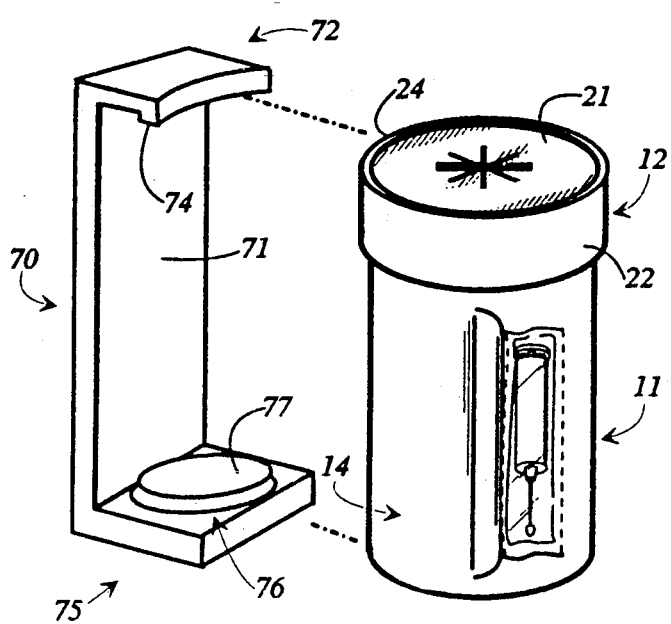
FIG. 7 is a perspective view of the present invention being mounted in another mounting bracket.
Figure 8:
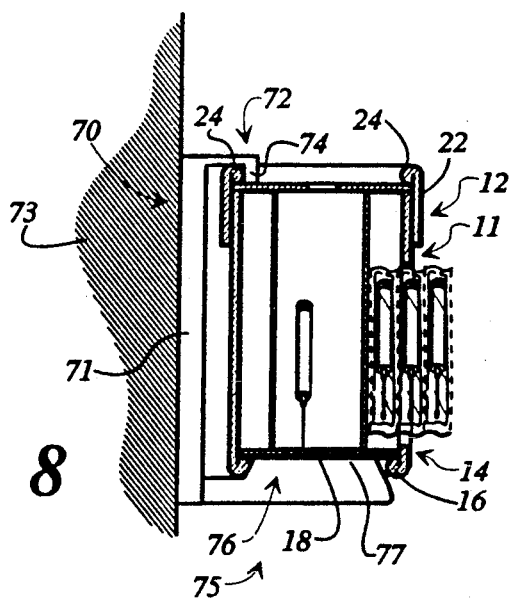
FIG. 8 is a side cross-sectional view of the mounting bracket of FIG. 7 with the container being mounted within the bracket.

Another embodiment 70 of the mounting bracket is shown in FIGS. 7 and 8, and can be preferably attached to a wall 73 (FIG. 8), and can be preferably attached to a wall 73 (FIG. 8) by adhesive or by multiple screws (not shown). As shown in FIGS. 7 and 8, the embodiment 79 comprises a longitudinal bracket 71 having a semi-circular upper arm 72 with a flange 74 for supporting the circular seat 24 rim of the container 11, when inserted into the mounting bracket. On the other end of the bracket 71, a base support 75 for the container 11 comprises a circular support arm 76 having a circular protrusion 77 which is of sufficient internal breadth to fit within the bottom wall 18 and the circular seat 16 of the container. The upper arm 72 and base support 75 are flexible support members allowing a used container to be easily replaced by a new container.

Figure 9:
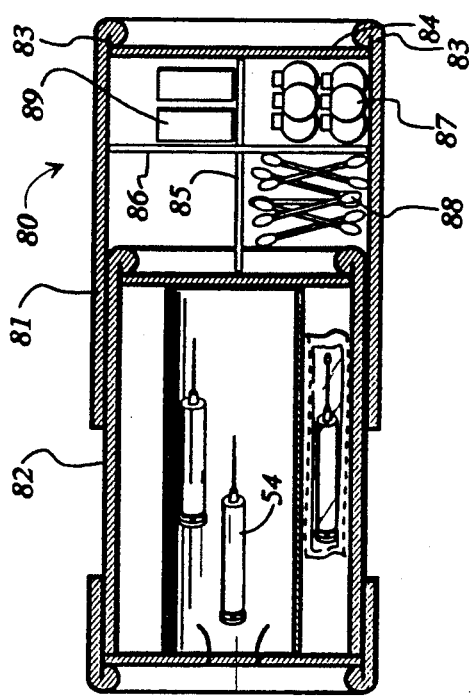
FIG. 9 is a side cross-sectional view of the container system showing a supply attachment connected to the container.

FIG. 9 shows a supply attachment 80 with a cylindrical side wall 81 of sufficient internal breadth to fit, such as by pressed-fit or friction-fit about a cylindrical side wall 82 of a container of any of the above described embodiments. The cylindrical side wall 81 of the attachment 80 has an inwardly projecting seat 83 which supports an end wall 84 of the supply attachment 80. The supply attachment can further include partitions or dividers such as 85 and 86 within the attachment for storing items, for example, items used by diabetic patients, such as insulin supplies 87, alcohol swabs 88, and test kits 89. This invention is particularly desireable because it offers the personal-use hypodermic syringe user, such as a diabetic, a complete system for dispensing, using and disposing of the hypodermic syringes. Moreover, this embodiment not only provides a safekeeping containment of the unused syringes so that they are not misplaced or removed from their designated location, it also provides a collecting chamber within the same embodiment in such a proximity, whereby there is little to no tendency for disposing of the hypodermic syringes elsewhere in a personal environment.

All of the above-described embodiments of this container system can be safely disposed of by several different methods. These disposal methods include throwing the containers with used syringes within the container into a generic household trash bag, incinerating or burning the container, and discarding the container by landfilling or autoclaving the container. The material of construction in any of the above-described embodiments can comprise plastic materials, such as thermoplastic resins, selected from the group consisting of: polypropylene, polyethylene, polystyrene, acrylonitrile-butadiene-styrene (ABS), and polycarbonate. An injection molding process is the preferred method of forming containers fabricated of such plastic materials.

The material of construction in any of the above-described embodiments can also comprise biodegradable, or otherwise known as nonpetroleum-based materials selected from the following group: natural cellulosic-based materials such as wood, cardboard, particle board and fiberboard, non-natural cellulosic materials, such as rayon, cellophane, and cellulose-nitrate and other materials, such as natural rubber and natural wax, which when burned, emit no more than trace amounts of sulfur or chlorine. These materials will form a clean-burning container, which may aid in the compliance of future incineration regulations for personal use-hypodermic syringes.

While this invention has been described in relation to these preferred embodiments, it will be apparent to those skilled in the art that the invention is susceptible to additional embodiments without departing from the spirit and scope of the invention. Therefore, it is intended that the invention not be limited except by the claims.

I claim:

1. A hypodermic needle syringe dispensing and disposing system for dispensing unused hypodermic needle syringes contained in a strip pack with the syringes positioned parallel to one another and for collecting used syringes comprising:
   a container including side wall means, end wall means, and one said end wall means being spaced from the other said end wall means a distance greater than the lengths of the syringes, and said side wall means defining a syringe storage chamber between said end wall means of a breadth sufficient to contain the strip pack of syringes,
   said side wall means defining an outlet opening from said chamber for the sequential passage therethrough of the syringes of the strip pack of syringes from within said chamber, and
   one of said end wall means defining opening means therein for the passage therethrough of used syringes,
   so that a strip pack of needle syringes is placed in the chamber and the free end of the strip pack is paid out through the outlet opening to dispense the syringes, and used syringes can be pushed from outside the container through said opening means of said end wall means into the chamber.

2. The syringe dispensing and disposing system of claim 1 and wherein said strip pack is arranged in a coil configuration and said opening means in said end wall means is aligned with the center of the coiled strip pack of needle syringes so that the used needle syringes can be pushed from outside the container into the central portion of the coiled strip pack of needle syringes.

3. The syringe dispensing and disposing system of claim 1 and wherein said side wall means is cylindrical.

4. The syringe dispensing and disposing system of claim 1 and wherein said strip pack is arranged in a coil with said needle syringes surrounded by strips of material bonded together on opposite sides of each needle syringe to seal each needle syringe individually.

5. The syringe dispensing and disposing system of claim 4 and wherein said strip pack includes perforations between each sealed needle syringe for allowing access to individual needle syringes.

6. The syringe dispensing and disposing system of claim 1 and wherein said strip pack includes indicia for determining the number of syringes left in said container.

7. The syringe dispensing and disposing system of claim 1 and wherein said container is sufficiently leak-resistant so as to contain the used syringes, including liquid medical wastes residual on the needles.

8. The syringe dispensing and disposing system of claim 1 and wherein said end wall means is needle puncture-resistant with respect to the syringes within said container.

9. The syringe dispensing and disposing system of claim 1 and wherein said opening means of said end wall means is scored to form weakened lines of separation for permitting a needle of a syringe to open the scored portion of the top wall.

10. The syringe dispensing and disposing system of claim 1 and wherein said container is cylindrical and comprises a cylindrical side wall turned in at its ends to form inwardly projecting seats, and said end wall means at opposite ends of said container supported by said seats.

11. The syringe dispensing and disposing system of claim 10 and wherein said container comprises a telescopic structure, including a body and a telescoping cover mounted about said body, with the telescoping cover connected to said body.

12. The syringe dispensing and disposing system of claim 1 and wherein said container is fabricated of thermoplastic resins selected from the group consisting of: polypropylene, polyethylene, polystyrene, acrylonitrile-butadiene-styrene, and polycarbonate.

13. The syringe dispensing and disposing system of claim 1 and wherein said container is fabricated of biodegradable material selected from the group consisting of: paper stock, cardboard, fiberboard, and particle board.

14. The syringe dispensing and disposing system of claim 1 and wherein the quantity of materials that form said container is matched with the volume of said chamber of said container so that the chamber will receive a predetermined number of needle syringes and so that the material of the container is sufficient to emit enough heat upon combustion to transform the syringes in the chamber into a substantially noncontaminated and noncombustible ash.

15. The syringe dispensing and disposing system of claim 1 and wherein said container, when burned, evolves no more than trace levels of chlorine or sulfur and which yields substantially only biodegradable ash upon combustion.

16. The syringe dispensing and disposing system of claim 1 and further comprising a mounting means including hollow support means and wherein said opening means of one of said end wall means can be opened to a sufficient breadth to receive said hollow support means of said mounting means, whereby the needle syringes can be pushed along their lengths through the hollow support means and into the chamber.

17. The syringe dispensing and disposing system of claim 1 and further comprising mounting means including a bracket and a support ring, and wherein said container is sized and shaped to be received in and supported by the bracket and support ring.

18. The syringe dispensing and disposing system of claim 16 and wherein said mounting means further includes a flexible support member extending adjacent said end wall of said container and engaging end wall for releasibly supporting said container within said mounting means.

19. The syringe dispensing and disposing system of claim 1 and further including an approximately cylindrical core member positioned in said chamber, and said strip pack arranged in a coil about said core member.

20. The syringe dispensing and disposing system of claim 19 and wherein said core member is radially expandable and is aligned with said opening means of said end wall means so that used needle syringes can be pushed along their lengths from outside the container through the opening means of one of the end wall means and into the core member within the chamber and the core member is radially expandable to accept more used needle syringes as the strip pack of syringes is dispensed from about the core member in the chamber.

21. The needle syringe dispensing and collecting system of claim 1 and further including a supply attachment mounted to said container for storing medication, swabs, test kits, and the like.

22. A hypodermic needle syringe dispensing and disposing system for dispensing unused hypodermic syringes contained in a strip pack with the syringes positioned parallel to one another and for collecting used syringes comprising:

a container including opposed end wall means and side wall means, said end wall means being spaced from each other a distance greater than the lengths of the syringes, and said side wall means defining a syringe storage chamber between said end wall means of a breadth sufficient to contain the strip pack of syringes, opening means in said container for the sequential passage therethrough of the syringes of the strip pack of syringes from within said chamber and for the passage therethrough of used syringes into said chamber, so that a strip pack of syringes is placed in the chamber and the free end of the strip pack is paid out through the opening means to dispense the syringes, and used syringes can be pushed from outside the container through said opening means into the chamber for collecting the used syringes.

23. The needle syringe dispensing and disposing system of claim 22 and wherein said container is sufficiently leak-resistant so as to contain the used syringes, including liquid medical wastes residual on the needles.

24. The needle syringe dispensing and disposing system of claim 22 and wherein at least one of said end wall means is needle puncture-resistant with respect to the syringes within said container.

* * * * *

UNITED STATES PATENT AND TRADEMARK OFFICE
CERTIFICATE OF CORRECTION

PATENT NO. : 5,152,394
DATED : Oct. 6, 1992
INVENTOR(S) : Hughes

It is certified that error appears in the above-identified patent and that said Letters Patent is hereby corrected as shown below:

On the cover page, in the heading, after "Hughes", add --et al.--.

On the cover page, line [75], add the second inventor's name and address: --L. Andrew Withers, Atlanta, Georgia--.

On the cover page, section [57] Abstract, line 4, change "place" to --placed--.

Column 3, line 6, change "desireable" to --desirable--.

Column 6, line 41, change "79" to --70--.

Column 6, line 54, change "pressed-fit" to --press-fitted--.

Column 6, line 63, change "desireable" to --desirable--.

Column 7, line 30, change "of" to --with--.

Signed and Sealed this

Ninth Day of November, 1993

Attest:

BRUCE LEHMAN

Attesting Officer

Commissioner of Patents and Trademarks